United States Patent [19]

Szilagyi nee Farago et al.

[11] 4,328,221
[45] May 4, 1982

[54] SUBSTITUTED STEROID-SPIRO-OXAZOLIDINONE DERIVATIVES AND A PROCESS FOR THE PREPARATION THEREOF

[75] Inventors: Katalin Szilágyi née Faragó; Sándor Sólyom; Lajos Toldy; Inge Schäfer; Eleonora Szondy; János Borvendég; Ilona Hermann née Szente, all of Budapest, Hungary

[73] Assignee: Richter Gedeon Vegyeszeti Gyar Rt., Budapest, Hungary

[21] Appl. No.: 220,139

[22] Filed: Dec. 24, 1980

[30] Foreign Application Priority Data

Dec. 28, 1979 [HU] Hungary .............................. GO 1463

[51] Int. Cl.³ ............................................. A61K 31/58
[52] U.S. Cl. .............................. 424/241; 260/239.55 R; 260/239.5
[58] Field of Search ............... 424/241; 260/239.55 R, 260/239.5

[56] References Cited

U.S. PATENT DOCUMENTS 4,180,505 12/1979 Sólyom et al. .................. 260/239.55

Primary Examiner—Elbert L. Roberts
Attorney, Agent, or Firm—Karl F. Ross

[57] ABSTRACT

Compounds of the formula (I) having aldosterone-antagonizing activity are disclosed

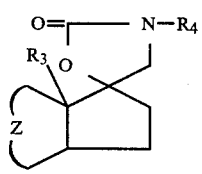

(I)

wherein
 $R_3$ and $R_4$ are each $C_1$ to $C_3$ alkyl; and
 Z is one of the following groups

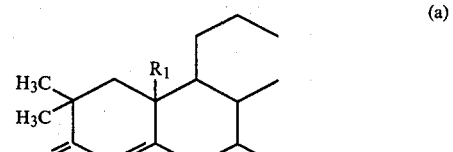

(a)

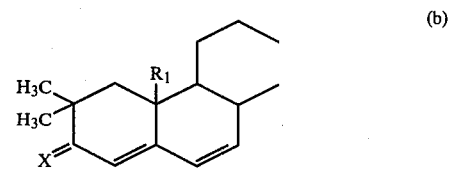

(b)

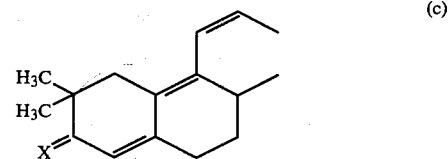

(c)

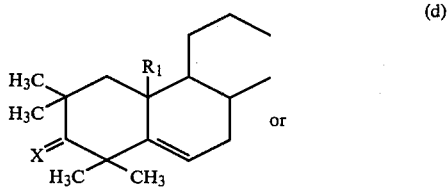

(d)

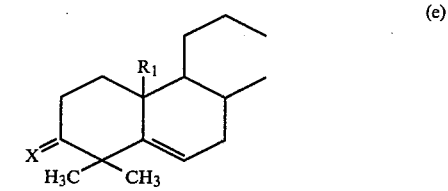

(e)

wherein
 $R_1$ is hydrogen or methyl;
 $R_6$ is hydrogen, $C_1$ to $C_3$ alkylthio or $C_2$ to $C_4$ acylthio; and
 X is oxo, hydroximino, $C_1$ to $C_3$ alkoxyimino, carboxy-alkoxyimino wherein the alkoxy has 2 to 4 carbon atoms or a salt-converted carboxy-alkoxyimino wherein the alkoxy has 2 to 4 carbon atoms.

13 Claims, No Drawings

SUBSTITUTED STEROID-SPIRO-OXAZOLIDINONE DERIVATIVES AND A PROCESS FOR THE PREPARATION THEREOF

The invention relates to steroid-spiro-oxazolidinone derivatives of the formula (I),

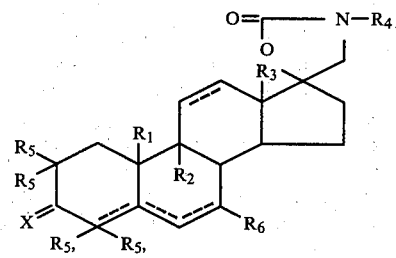

wherein
$R_1$ is hydrogen or methyl,
$R_2$ is hydrogen, or
$R_1$ and $R_2$ together form a valence bond,
$R_3$ is $C_{1-3}$ alkyl,
$R_4$ is $C_{1-3}$ alkyl or $C_{2-4}$ alkenyl,
$R_5$ and $R_{5'}$ are each hydrogen or methyl group with at least one of the $R_5$ and $R_{5'}$ substituent pairs always representing two methyl groups,
$R_6$ is hydrogen, $C_{1-3}$ alkylthio or $C_{2-4}$ acylthio, the dotted lines represent additional valence bonds optionally present, and if $R_5$ is methyl, there is a double bond between the carbon atoms in positions 4 and 5, and additional double bonds can be between the carbon atoms in positions 6 and 7, 9 and 10 (for these compounds $R_1$ and $R_2$ form together a valence bond) and 11 and 12, and if $R_5$ is hydrogen or methyl and at the same time $R_{5'}$ is methyl, there is a double bond between the carbon atoms in positions 5 and 6, and if $R_6$ is $C_{1-3}$ alkylthio or $C_{2-4}$ acylthio group, only a bond lies between the carbon atoms in positions 6 and 7, furthermore X is oxygen, hydroxyimino, $C_{1-3}$ alkoxyimino, $C_{2-4}$ carboxyalkoxyimino or a salt-converted $C_{2-4}$ carboxyalkoxyimino,
and pharmaceutical compositions containing the same. The invention also relates to a process for the preparation of such compounds.

The compounds of the formula (I) may exist in the form of various stereoisomers and isomeric mixtures, all of them being within the scope of the invention.

The compounds of the formula (I) are new and possess valuable biological effects. Some representatives of these new compounds exert outstanding anti-mineralocorticoid effects.

It is known that aldosterone, a hormone of the adrenal cortex, causes sodium retention and stimulates the excretion of potassium. In certain pathological states of the adrenal gland hyperaldosteronism occurs and responsible for several oedemas of hepatic, renal and cardiac origin. In such instances aldosterone always reaches a high concentration in the blood.

Compounds with aldosterone-antagonizing effects are capable of inhibiting the harmful effects of the hormone exerted in these pathological states. These compounds enhance the excretion of sodium ions through the tubular cells of the kidney, thereby evacuating the oedemas. Thus the aldosterone-antagonizing agents exert diuretic effects, and represent a particularly important group of diuretics. These compounds are used in therapy for the treatment of arterial hypertension and cardiac insufficiency for example.

The new steroid derivatives of the formula (I) are prepared according to the invention so that a compound of the formula (II)

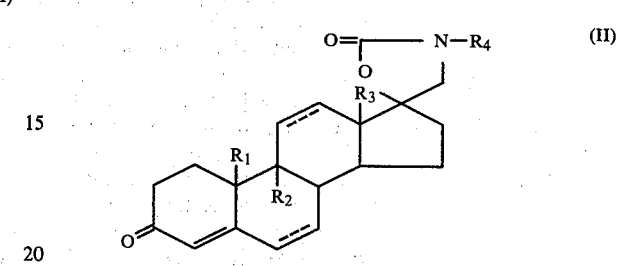

wherein $R_1$, $R_2$, $R_3$, $R_4$ and the dotted lines are as defined above, is reacted with a methyl halide in the presence of an alkaline agent, and, if desired, a resulting compound of the formula (I), wherein X is oxygen, is converted into a derivative containing one or two additional double bonds, and/or, if desired, a $C_{1-3}$ alkyl mercaptan or a $C_{2-4}$ thiocarboxylic acid is coupled by addition on the double bond in positions 6 and 7, and/or, if desired, a compound of the formula (I), wherein X stands for oxygen, is converted into the respective oxime derivative wherein X stands for a hydroxyimino, $C_{1-3}$ alkoxyimino or $C_{2-4}$ carboxyalkoxyimino group, and/or, if desired, a compound of the general formula (I), wherein X stands for a carboxyalkoxyimino group is converted into its salt.

The optional conversions listed above can be performed by methods known per se.

According to a preferred method of the invention methyl iodide is used as the methyl halide, and an alkali metal alcoholate, such as potassium tert.-butoxide, is used as the alkaline agent. Methylation is performed at or below room temperature.

When α,β-unsaturated 3-oxo-steroid-17-spiro-oxazolidinone type compounds, which may contain optionally one or more additional conjugated double bonds, are methylated according to the invention at low temperatures, preferably below −30° C., the respective 2,2-dimethyl derivatives or mixtures of the 2,2-dimethyl and 2,2,4,4-tetramethyl derivatives are obtained. If methylation is performed at low temperatures, it is preferred to conduct the reaction in ether-type solvents, such as tetrahydrofuran.

When α,β-unsaturated 3-oxo-steroid-17-spiro-oxazolidinones are methylated at or near room temperature, the respective 4,4-dimethyl derivatives are obtained as main products. In such instances the reaction is performed preferably at 0° to +30° C., e.g. in tert.-butylalcohol.

The products obtained in the methylation step can be separated by methods known in the art, such as by pouring the reaction mixture into water and then extracting the products. The individual compounds can be separated from each other e.g. by fractional crystallization or chromatography.

Optionally one or two additional double bonds may be introduced into the compounds obtained by low temperature methylation. Thus e.g. the 2,2-dimethyl-3- oxo-steroid-4-ene-17-spiro-oxazolidinones can be oxidized with a benzoquinone derivative to obtain the respective $\Delta^{6(7)}$ compounds. It is preferred to use chloranil or dichloro-dicyano-benzoquinone as the benzoquinone derivative, and the respective 2,2-dimethyl-3-oxo-4-ene-steroid or its enol ether can be used as starting substance in the oxidation step.

When 19-nor-2,2-dimethyl-3-oxo-4-ene-steroids containing double bonds in positions 9,10 and 11,12 are to be prepared, the compound to be methylated may already contain these double bonds, however, the double bonds can also be introduced into the molecule after methylation. Methods well known in the steroid chemistry can be used for this purpose [see e.g. Fried, J., Edwards, I. A.: Organic Reactions in Steroid Chemistry, Vol. 1, Van Nostrand Reinhold Comp., New York, 1972, pages 266 and 314]. Thus e.g. the double bond in position 4,5 can be shifted into position 5,10 by enamine formation and subsequent hydrolysis under mild acidic conditions, and brominating the resulting 2,2-dimethyl-3-oxo-5(10)-ene-spiro-oxazolidinone derivative in the presence of pyridine to obtain a 3-oxo-4,9(10)-diene structure. Similarly, a 2,2-dimethyl-3-oxo-4,9(10)-diene type spiro-oxazolidinone may be subjected to enamine formation and then hydrolyzed, and the resulting 3-oxo-5(10),9(11)-diene compound may be oxidized with dichlorodicyano-benzoquinone to obtain a 2,2-dimethyl-3-oxo-4,9(10),11-triene structure.

The methods discussed above for the introduction of one or two additional conjugated double bonds into the methylated compounds are also embraced by the scope of the invention.

If desired, a sulfur-containing substituent can be attached to the carbon atom in position 7. These derivatives are prepared preferably from the respective 2,2-dimethyl-3-oxo-steroid-4,6-diene-17-spiro-oxazolidinones by coupling them with a mercaptan or a thiocarboxylic acid. The addition is performed by heating the starting substance in an excess of the reactant. When a mercaptan is used as reactant, it is preferred to add a basic catalyst, such as piperidine, to the reaction mixture.

If desired, a methylated spiro-oxazolidinone can be converted into the respective oxime by heating the 3-oxo-steroid and the appropriate hydroxylamine salt in the presence of an acid binding agent. According to a preferred method sodium acetate is applied as acid binding agent and the reaction is conducted in aqueous alcohol, or pyridine is applied which serves both as acid binding agent and as solvent medium.

Of the oxime derivatives the 3-carboxyalkoxyiminospiro compounds, prepared by applying carboxyalkoxamine salts as reactants, are preferred. These compounds are soluble in buffer solutions and can be converted into salts by treating them with an equivalent amount of an alkali. Thereby the water solubility of the starting substance can be improved, which is an essential factor with respect to therapeutical use.

The compounds of the formula (II) used as starting substances in the process of the invention as well as their preparation are described in the Belgian Pat. No. 864,689.

The aldosterone-antagonizing effects of the new compounds according to the invention were investigated by two methods.

The first test series was carried out on rats according to the method of C. M. Kagawa [C. M. Kagawa et al.: J. Pharmacology Exp. Ther. 126, 123 (1959)]. The adrenal gland of the animals was removed 18 hours before treatment. The compound under examination was administered together with deoxycorticosterone acetate (DOCA), a substance capable of supplementing the aldosterone effect, and the sodium and potassium contents of the urine were determined by flame photometry. In the comparative test an oral dose of 480 μg of spironolactone (17α-carboxyethyl-17β-hydroxy-7α-acetylthio-androst-4-ene-3-one lactone) was administered. The results were evaluated by calculating the log (10 Na$^+$/K$^+$) values. The results are summarized in Table 1.

The second test series ("sodium balance" test) was carried out on selected male rats weighing 230 to 250 g. The test was performed according to the method of Holmann [Arch. Exp. Path. u. Pharmak. 247, 419 (1964)].

The rats were loaded with an intravenous infusion of 0.2% sodium chloride solution rendered isoosmotic with glucose, and the sodium excreting capacity of the kidney was observed for 24 hours. It was found that the amount of Na$^+$ introduced by infusion was in equilibrium with that excreted with the urine between the 4th and 13th hours.

The tests were then performed on the following three groups:
Group 1—controls
Group 2—mineralocorticoid group
Group 3—antagonized mineralocorticoid group The animals of the second group received a subcutaneous dose of 6.25 μg of deoxycorticosterone acetate (DOCA) simultaneously with the start of infusion. By a single dose of the mineralocorticoid hormone of the adrenal cortex hyperaldosteroinism was provoked on the animals. The animals of Group 3 also received a subcutaneous dose of 6.25 μg of DOCA, and then they were treated with 5.5 mg of spironolactone (reference substance) or the compound under examination in the 2nd hour of the test period.

The Na$^+$ concentration of the urine (expressed in units of $10^{-6}$ mol/ml) and the amount of Na$^+$ excreted hourly (expressed in units of $10^{-6}$ mol/h) were determined, and the extent of sodium retention was calculated from the data. Sodium retention, expressed as percent of sodium introduced, is given in Table 2.

The daily dose of the compounds of formula I for adults amounts to 50 to 400 mg per body weight.

TABLE 1

| Examination of antimineralocorticoid effects on rats according to the method of Kagawa | | | |
|---|---|---|---|
| Compound tested | Dose μg/animal p.o. | No. of animals | log (10Na$^+$/K$^+$) |
| 2,2-Dimethyl-3-oxo-oestr-4-ene-17S-spiro-5'-(2'-oxo-3'-methyl-oxazolidine) | 480 | 14 | 1.08 |
| 2,2-Dimethyl-3-oxo-4-androstene-17S-spiro-5'-(2'-oxo-3'-methyl-oxazolidine) | 480 | 8 | 1.07 |
| 2,2-Dimethyl-3-oxo-androsta-4,6-diene-17S-spiro-5'- | | | |

TABLE 1-continued
Examination of antimineralocorticoid effects on rats according to the method of Kagawa

| Compound tested | Dose µg/animal p.o. | No. of animals | log (10Na$^+$/K$^+$) |
|---|---|---|---|
| (2'-oxo-3'-methyl-oxazolidine) | 480 | 8 | 1.66 |
| 13β-Ethyl-2,2-dimethyl-3-oxo-gona-4,9(10),11-triene-17S-spiro-5'-(2'-oxo-3'-methyl-oxazolidine) | 480 | 8 | 1.18 |
| 13β-Ethyl-4,4-dimethyl-3-oxo-gon-5-ene-17S-spiro-5'-(2'-oxo-3'-methyl-oxazolidine) | 480 | 6 | 1.26 |
| 13β-Ethyl-2,2,4,4-tetramethyl-3-oxo-gon-5-ene-17S-spiro-5'-(2'-oxo-3'-methyl-oxazolidine) | 480 | 8 | 1.10 |
| DOCA | — | 28 | 0.78 |
| Spironolactone | 480 | 21 | 1.21 |

Remark: DOCA was administered in a subcutaneous dose of 12.5 µg/animal.

TABLE 2
Examination of antimineralocorticoid effects on rats according to the method of Holmann

| Compound | Dose per animal s.c. | No. of animals | Sodium retention, % |
|---|---|---|---|
| Control | — | 6 | 22.68 |
| DOCA | 6.25 µg | 10 | 66.55 |
| DOCA + Spironolactone | 6.25 µg + 5.5 mg | 9 | 5.36 |
| DOCA + 2,2-Dimethyl-3-oxo-androsta-4,6-diene-17S-spiro-5'-(2'-oxo-3'-methyl-oxazolidine) | 6.25 µg + 5.5 mg | 7 | 4.50 |
| DOCA + 13β-Ethyl-2,2-dimethyl-3-oxo-gona-4,9(10),11-triene-17S-spiro-5'-(2'-oxo-3'-methyl-oxazolidine) | 6.25 µg + 5.5 mg | 11 | 16.16 |

Some of the compounds strongly inhibit the mineralocorticoid effect of DOCA. In this respect the following derivatives proved to be particularly preferred:

2,2-dimethyl-3-oxo-androsta-4,6-diene-17S-spiro-5'-(2'-oxo-3'-methyl-oxazolidine), 13β-ethyl-2,2-dimethyl-3-oxo-gona-4,9(10),11-triene-17S-spiro-5'-(2'-oxo-3'-methyl-oxazolidine), and 13β-ethyl-4,4-dimethyl-3-oxo-gon-5-ene-17S-spiro-5'-(2'-oxo-3'-methyl-oxazolidine).

These compounds exert the same or even stronger aldosterone inhibiting effect as spironolactone, applied as reference substance but, surprisingly, they do not have hormonal effects.

The compounds applied so far in the treatment of hyperaldosteronism, such as spironolactone, have the significant disadvantage that they exert certain sexual-specific side effects as well, thus, sooner or later, certain disturbances may appear during the usual prolonged treatment period.

The disturbances caused by the antiandrogenic and gestagenic effects of the known antialdosterone substances are particularly disadvantageous.

The antiandrogenic effects of the new compounds according to the invention were examined by the modified Dorfman method [Dorfman, R. I., Stevens, D. F.: Endocrinology 67, 394 (1960)].

Infantile castrated male rats, weighing 50 g, were treated for 7 days with subcutaneous daily dosages of 50 µg of testosterone propionate. The compounds under examination were administered in subcutaneous daily doses of 1 mg simultaneously with testosterone propionate.

On the 8th day of treatment the animals were sacrificed, the ventral prostatic lobe and the seminal vesicle were removed and weighed on a torsion balance.

It is known that substances with antiandrogenic effects suppress the weight gain of accessory sexual glands provoked by testosterone propionate. The extent of inhibiting effect can be expressed in percents, regarding the weight gain of the glands stimulated by testosterone propionate as 100%.

According to the above test spironolactone, when administered for 7 days in daily doses of 0.5 or 1.0 mg/animal, inhibits the weight gain of ventral prostatic lobe by 35% or 45%, respectively, whereas on the seminal vesicle an inhibiting effect of 38% or 54%, respectively, can be observed. On the contrary, 2,2-dimethyl-3-oxo-androsta-4,6-diene-17S-spiro-5'-(2'-oxo-3'-methyl-oxazolidine) and 13β-ethyl-2,2-dimethyl-3-oxo-gona-4,9(10),11-triene-17S-spiro-5'-(2'-oxo-3'-methyl-oxazolidine) have no antiandrogenic effects when administered in daily doses of 1 mg/animal.

The gestagenic effects of the new compounds according to the invention were examined by the method of C. Clauberg [C. Clauberg: Zentralblatt Gynaekol. 54, 2757 (1930)].

Infantile female New Zealand rabbits were treated for 5 days with subcutaneous daily doses of 5 µg of oestradiol. Thereafter the animals received subcutaneously under examination the compound for 5 days. Samples were taken from both uteral horns at two different heights, the samples were processed for histological evaluation and then evaluated according to McPhail.

In this test spironolactone caused a slight gestagenic effect in a dose of 5×1 mg/kg, whereas a significant gestagenic effect appeared after treating with 5×5 mg/kg of spironolactone (the McPhail indices were 0.3 and 2.0, respectively). On the contrary, 2,2-dimethyl-3-oxo-androsta-4,6-diene-17S-spiro-5'-(2'-oxo-3'-methyl-oxazolidine) and 13β-ethyl-2,2-dimethyl-3-oxo-gona-4,9(10),11-triene-17S-spiro-5'-(2'-oxo-3'-methyl-oxazolidine) proved to be inactive in the same doses.

The compounds of the formula (I) can be converted into pharmaceutical compositions for enteral or parenteral administration. These pharmaceutical compositions may be solid or liquid preparations (such as tablets, coated tablets, capsules, pills, suppositories, emulsions, suspensions, injectable solutions, etc.) and can be prepared by conventional methods, utilizing pharmaceutically acceptable inert carriers (such as talc, lactose, magnesium stearate, starch, water, vegetable oils, waxes, etc.) and/or other additives (such as preservatives, stabilizers, flavoring agents, surfactants, salts for adjusting the osmotic pressure, etc.).

The invention is elucidated in detail with the aid of the following non-limiting Examples.

EXAMPLE 1

2,2-Dimethyl-3-oxo-4-androstene-17S-spiro-5'-(2'-oxo-3'-methyl-oxazolidine)

4 g of 3-oxo-4-androstene-17S-spiro-5'-(2'-oxo-3'-methyl-oxazolidine) are dissolved in a mixture of 25 ml of tetrahydrofuran and 12.5 ml of methyl iodide, and the solution is cooled to −60° C. A suspension of 6 g of potassium tert.-butoxide in 30 ml of tetrahydrofuran is added to the stirred solution under nitrogen atmosphere at such a rate that the temperature does not raise above −60° C. When the addition is complete the mixture is stirred at −60° C. for one hour, thereafter the reaction mixture is poured into 600 ml of ice water and the product is extracted with dichloromethane. The extract is washed with water, dried over magnesium sulfate, evaporated, and the residue is recrystallized from ethyl acetate. 2.34 g of 2,2-dimethyl-3-oxo-4-androstene-17S-spiro-5'-(2'-oxo-3'-methyl-oxazolidine) are obtained; m.p.: 188°–190° C.

$[\alpha]_D^{20} = +8.05°$ (c=0.5%, in chloroform).
UV $\lambda_{max.}^{EtOH} = 239$ nm (E=15,000).

EXAMPLE 2

2,2-Dimethyl-3-oxo-androsta-4,6-diene-17S-spiro-5'-(2'-oxo-3'-methyl-oxazolidine)

Method "A":

4.76 g of 2,2-dimethyl-3-oxo-4-androstene-17S-spiro-5'-(2'-oxo-3'-methyl-oxazolidine), prepared as described in Example 1, are dissolved in 90 ml of methanol. 3.16 g of chloranil and a catalytic amount (about 20 mg) of p-toluenesulfonic acid are added to the solution, and the mixture is boiled for 15 hours. The reaction mixture is evaporated to one-third of its original volume under reduced pressure, the volume of the concentrate is readjusted to the original one with water, and the resulting mixture is extracted three times with dichloromethane. The dichloromethane solutions are combined and washed with 1 n aqueous sodium hydroxide solution containing 3% of sodium dithionite until the wash remains colorless. The organic phase is washed then with water, dried over magnesium sulfate, evaporated, and the 3.74 g of crude crystalline residue are recrystallized from ethyl acetate. Pure 2,2-dimethyl-3-oxo-androsta-4,6-diene-17S-spiro-5'-(2'-oxo-3'-methyl-oxazolidine) is obtained; m.p.: 225°–228° C.

$[\alpha]_D^{20} = -31.8°$ (c=0.5%, in chloroform).
UV $\lambda_{max.}^{EtOH} = 281$ nm (E=23,600).

Method "B":

3.97 g of 3-oxo-androsta-4,6-diene-17S-spiro-5'-(2'-oxo-3'-methyl-oxazolidine) are dissolved in a mixture of 25 ml of tetrahydrofuran and 12.5 ml of methyl iodide, and the solution is cooled to −60° C. A suspension of 6 g of potassium tert.-butoxide in 30 ml of tetrahydrofuran is added to the stirred solution under nitrogen atmosphere at such a rate that the temperature does not rise above −60° C. When the addition is complete the mixture is stirred at −60° C. for one hour, thereafter the reaction mixture is poured into 600 ml of ice water and the product is extracted with dichloromethane.

The dichloromethane extract is washed with water, dried over magnesium sulfate, evaporated, and the crystalline crude product is recrystallized from ethyl acetate. 2.72 g of pure 2,2-dimethyl-3-oxo-androsta-4,6-diene-17S-spiro-5'-(2'-oxo-3'-methyl-oxazolidine) are obtained; the compound is identical with the product obtained according to method "A".

EXAMPLE 3

2,2-Dimethyl-3-oxo-7α-acetylthio-4-androstene-17S-spiro-5'-(2'-oxo-3'-methyl-oxazolidine)

A suspension of 2 g of 2,2-dimethyl-3-oxo-androsta-4,6-diene-17S-spiro-5'-(2'-oxo-3'-methyl-oxazolidine), prepared as described in Example 2, in 2 ml of thioacetic acid is heated on a steam bath for 2 hours. The excess of thioacetic acid is evaporated under reduced pressure, and the residue is triturated with a 1:1 mixture of ethyl acetate and isopropyl ether. The crude product is filtered off and recrystallized from ethyl acetate. 1.22 g of pure 2,2-dimethyl-3-oxo-7α-acetyl-thio-4-androstene-17S-spiro-5'-(2'-oxo-3'-methyl-oxazolidine) are obtained; m.p.: 238°–242° C.

$[\alpha]_D^{20} = -88.30°$ (c=0.5%, in chloroform).
UV $\lambda_{max.}^{EtOH} = 237$ nm (E=18,900).

EXAMPLE 4

2,2-Dimethyl-3-oxo-7α-ethylthio-4-androstene-17S-spiro-5'-(2'-oxo-3'-methyl-oxazolidine)

2.4 g of 2,2-dimethyl-3-oxo-androsta-4,6-diene-17S-spiro-5'-(2'-oxo-3'-methyl-oxazolidine), prepared as described in Example 2, are suspended in 15 ml of ethyl mercaptan, and 1.5 ml of piperidine are added. The reaction mixture is heated on a steam bath for 10 hours, then cooled and allowed to stand in a refrigerator. The separated crystalline crude product is filtered off and recrystallized from ethanol. 1.44 g of pure 2,2-dimethyl-3-oxo-7α-ethylthio-4-androstene-17S-spiro-5'-(2'-oxo-3'-methyl-oxazolidine) are obtained; m.p.: 262°–263° C.

$[\alpha]_D^{20} = -78.3°$ (c=0.5%, in chloroform).
UV $\lambda_{max.}^{EtOH} = 239$ nm (E=16,100).

EXAMPLE 5

2,2-Dimethyl-3-oxo-oestr-4-ene-17S-spiro-5'-(2'-oxo-3'-methyl-oxazolidine) and
2,2,4,4-tetramethyl-3-oxo-oestr-5-ene-17S-spiro-5'-(2'-oxo-3'-methyl-oxazolidine)

A solution of 3.43 g of 3-oxo-oestr-4-ene-17S-spiro-5'-(2'-oxo-3'-methyl-oxazolidine) in a mixture of 30 ml of tetrahydrofuran and 10 ml of methyl iodide is cooled to −60° C., and a suspension of 5.0 g of potassium tert.-butoxide in 10 ml of tetrahydrofuran, previously cooled to −30° C., is added to the stirred solution under nitrogen atmosphere. The reaction mixture is stirred at −60° C. for 5 hours and then poured into 600 ml of water. The product is extracted with ethyl acetate. The ethyl acetate solution is washed with water and then with 5% aqueous sodium chloride solution until neutral, dried and evaporated. The oily residue is subjected to chromatography on 300 g of silica gel, using a 3:1 mixture of chloroform and ethyl acetate as eluting agent.

The pure effluent fractions which contain the first eluted substance are combined and evaporated. 0.66 g of crude crystalline 2,2,4,4-tetramethyl-3-oxo-oestr-5-ene- 17S-spiro-5'-(2'-oxo-3'-methyl-oxazolidine) are obtained; this compound melts at 184°–185° C. after recrystallization from ethyl acetate. (The UV spectrum of the compound contains no absorption band between 220 and 300 nm).

The pure effluent fractions which contain the second eluted substance are combined and evaporated. 1.00 g of crystalline 2,2-dimethyl-3-oxo-oestr-4-ene-17S-spiro-5'-(2'-oxo-3'-methyl-oxazolidine) is obtained. This compound melts at 221°–223° C. after recrystallization from ethyl acetate.

$[\alpha]_D^{20} = -13.1°$ (c=0.5%, in chloroform).
UV $\lambda_{max.}^{EtOH} = 238$ nm (E=16,500).

EXAMPLE 6

3-Oxo-4,4-dimethyl-oestr-5-ene-17S-spiro-5'-(2'-oxo-3'-methyl-oxazolidine)

2.44 g of potassium tert.-butoxide are dissolved in 24 ml of tert.-butanol, the solution is cooled to 8° C., and 1.85 g of 3-oxo-oestr-4-ene-17S-spiro-5'-(2'-oxo-3'-methyl-oxazolidine) are introduced under stirring. The reaction mixture turns yellow. After 10 minutes a solution of 1.40 ml of methyl iodide in 5 ml of tetrahydrofuran is added dropwise to the mixture within about 10 minutes. Stirring is continued for 4 hours at 8° C. and then the reaction mixture is poured into 1 liter of ice water.

The product is extracted thrice with 200 ml of ethyl acetate, each, the extracts are combined, washed with water until neutral, dried and evaporated. The crystalline crude product is dissolved in 100 ml of ethanol under heating, and the solution is concentrated to a final volume of about 30 ml. 0.69 g of pure 3-oxo-4,4-dimethyl-oestr-5-ene-17S-spiro-5'-(2'-oxo-3'-methyl-oxazolidine) separate from the solution; m.p.: 217°–218° C.

$[\alpha]_D^{20} = -61.7°$ (c=1%, in chloroform).

EXAMPLE 7

13$\beta$-Ethyl-2,2-dimethyl-3-oxo-gon-4-ene-17S-spiro-5'-(2'-oxo-3'-methyl-oxazolidine) and
13$\beta$-ethyl-2,2,4,4-tetra-methyl-3-oxo-gon-5-ene-17S-spiro-5'-(2'-oxo-3'-methyl-oxazolidine)

A solution of 5.0 g of 13$\beta$-ethyl-3-oxo-gon-4-ene-17S-spiro-5'-(2'-oxo-3'-methyl-oxazolidine) in a mixture of 40 ml of tetrahydrofuran and 20 ml of methyl iodide is cooled to −70° C., and a suspension of 10 g of potassium tert.-butoxide in 50 ml of tetrahydrofuran is added to the stirred solution under nitrogen atmosphere. The addition requires 10 minutes. After 25 minutes a suspension of additional 7 g of potassium tert.-butoxide in 30 ml of tetrahydrofuran is introduced, and the mixture is stirred then at −60° C. for 15 minutes. Thereafter the reaction mixture is decomposed with 30 ml of a 1:1 mixture of concentrated hydrochloric acid and water, and the mixture is poured into 400 ml of water.

The product is extracted thrice with 150 ml of ethyl acetate, each. The extracts are combined, washed thrice with 100 ml of water, each, twice with 50 ml of 2% aqueous sodium thiosulfate solution, each, and then again with 50 ml of water, dried and evaporated. The resulting oily residue, weighing 6.0 g, is subjected to chromatography on 480 g of silica gel, using a 3:1 mixture of chloroform and ethyl acetate as eluting agent.

The pure effluent fractions which contain the first eluted substance are combined and evaporated. An oily substance is obtained which crystallizes when triturated with isopropyl ether. The resulting 1.56 g of crude 13$\beta$-ethyl-2,2,4,4-tetra-methyl-3-oxo-gon-5-ene-17S-spiro-5'-(2'-oxo-3'-methyl-oxazolidine) are recrystallized from ethanol; m.p.: 191°–192° C.

$[\alpha]_D^{20} = -7.6°$ (c=0.5%, in chloroform).

Elution is continued, the pure fractions which contain a more polar substance are combined, and the solution is evaporated. The crystalline residue is washed with isopropyl ether, and the resulting 1.81 g of 13$\beta$-ethyl-2,2-dimethyl-3-oxo-gon-4-ene-17S-spiro-5'-(2'-oxo-3'-methyl-oxazolidine) are recrystallized from 6 ml of ethanol. 1.29 g of the pure substance are obtained; m.p.: 223°–225° C.

$[\alpha]_D^{20} = -9.6°$ (c=0.5%, in chloroform).
UV $\lambda_{max.}^{EtOH} = 238$ nm (E=15,600).

EXAMPLE 8

13$\beta$-Ethyl-4,4-dimethyl-3-oxo-gon-5-ene-17S-spiro-5'-(2'-oxo-3'-methyl-oxazolidine)

1.22 g of potassium tert.-butoxide are dissolved in 14 ml of tert.-butanol, and 1.0 g of 13$\beta$-ethyl-3-oxo-gon-4-ene-17S-spiro-5'-(2'-oxo-3'-methyl-oxazolidine) is added to the stirred solution at 10° C. After 10 minutes 1.35 ml of methyl iodide are added dropwise to the mixture. The reaction mixture is stirred for 4 hours and then concentrated to the half of its original volume under reduced pressure. The concentrate is diluted with water and the product is extracted with ethyl acetate. The ethyl acetate solution is washed with water until neutral, dried and then evaporated. The oily residue is subjected to chromatography on 40 g of silica gel, using a 3:1 mixture of chloroform and ethyl acetate as eluting agent. The fractions which contain the main product are combined and evaporated, and the resulting 0.58 g of crude product is crystallized from isopropyl ether. The product, 13$\beta$-ethyl-4,4-dimethyl-3-oxo-gon-5-ene-17S-spiro-5'-(2'-oxo-3'-methyl-oxazolidine), melts at 168°–170° C.

$[\alpha]_D^{20} = -56.6°$ (c=0.5%, in chloroform).

EXAMPLE 9

13$\beta$-Ethyl-2,2-dimethyl-3-oxo-gona-4,9(10),11-triene-17S-spiro-5'-(2'-oxo-3'-methyl-oxazolidine)

2.77 g of 13$\beta$-ethyl-3-oxo-gona-4,9(10),11-triene-17S-spiro-5'-(2'-oxo-3'-methyl-oxazolidine) are dissolved in a mixture of 50 ml of tetrahydrofuran and 6 ml of methyl iodide, and the solution is cooled to −70° C. A suspension of 4.1 g of potassium tert.-butoxide in 25 ml of tetrahydrofuran, cooled to −40° C., are added dropwise to the stirred solution within about 10 minutes. After a reaction time of 1.5 hours the mixture is poured into 800 ml of saturated aqueous ammonium chloride solution, and the product is extracted with four portions of 100 ml of ethyl acetate, each. The extracts are combined, washed twice with 40 ml of water, each, and then with 20 ml of a 2% aqueous sodium thiosulfate solution, dried and evaporated. The oily residue is subjected to chromatography on 400 g of silica gel, using a 3:1 mixture of chloroform and ethyl acetate as eluting agent. The pure fractions which contain the product are combined and evaporated. The resulting 1.67 g of crystalline substance are recrystallized from ethyl acetate to obtain 13$\beta$-ethyl-2,2-di-methyl-3-oxo-gona-4,9(10),11-triene-17S-spiro-5'-(2'-oxo-3'-methyl-oxazolidine) melting at 176°–179° C.

$[\alpha]_D^{20} = +95.1°$ (c=0.5%, in chloroform).
UV $\lambda_{max.}^{EtOH} = 234$ nm (E=6000), 335 nm (E=30,000).

EXAMPLE 10

2,2-Dimethyl-3-oximino-androsta-4,6-diene-17S-spiro-5'-(2'-oxo-3'-methyl-oxazolidine)

1.2 g of 2,2-dimethyl-3-oxo-androsta-4,6-diene-17S-spiro-5'-(2'-oxo-3'-methyl-oxazolidine), prepared as disclosed in Example 2, are suspended in 12 ml of ethanol, and a solution of 0.3 g of hydroxylamine hydrochloride and 0.38 g of sodium acetate in 2 ml of water is added to the suspension. The reaction mixture is stirred and boiled for 2 hours, then the solvent is evaporated under reduced pressure. The residue is triturated with water, the precipitate is filtered off, washed with water and dried. The crude product is recrystallized from methanol to obtain 0.83 g (66%) of 2,2-dimethyl-3-oximino-androsta-4,6-diene-17S-spiro-5'-(2'-oxo-3'-methyl-oxazolidine); m.p.: 267°–272° C.

UV $\lambda_{max.}^{EtOH}$=277 nm (E=24,000).

EXAMPLE 11

2,2-Dimethyl-3-carboxymethoxyimino-androsta-4,6-di-ene-17S-spiro-5'-(2'-oxo-3'-methyl-oxazolidine)

3 g of 2,2-dimethyl-3-oxo-androsta-4,6-diene-17S-spiro-5'-(2'-oxo-3'-methyl-oxazolidine), prepared as described in Example 2, are dissolved in 30 ml of pyridine. 1.2 g of aminoxyacetic acid hemihydrochloride are added to the solution, and the mixture is heated on a steam bath for 3 hours. The reaction mixture is cooled and poured into 600 ml of water containing 40 ml of concentrated hydrochloric acid. After one hour of standing the separated precipitate is filtered off and washed with water until neutral. The resulting 3.21 g (89%) of 2,2-dimethyl-3-carboxymethoxyimino-androsta-4,6-diene-17S-spiro-5'-(2'-oxo-3'-methyl-oxazolidine) are triturated with isopropyl ether and washed on the filter. The product melts at 210°–213° C.

UV $\lambda_{max.}^{EtOH}$=281 nm (E=23,200).

EXAMPLE 12

3-Oxo-4,4-dimethyl-5-androstene-17S-spiro-5'-(2'-oxo-3'-methyl-oxazolidine)

3.15 g of potassium tert.-butoxide are dissolved in 30 ml of tert.-butanol, and 2.6 g of 3-oxo-4-androstene-17S-spiro-5'-(2'-oxo-3'-methyl-oxazolidine) are added to the solution at 10° C. under stirring. After 10 minutes 3.5 ml of methyl iodide are added dropwise to the mixture. The reaction mixture is stirred for 2 hours, then concentrated under reduced pressure, and the residue is triturated with water. The crude product is filtered off, dried and then subjected to chromatography on 100 g of silica gel, using a 3:1 mixture of chloroform and ethyl acetate as eluting agent. The fractions which contain the main product are combined, evaporated, and the resulting 1.33 g of crude product are recrystallized from dioxane. 3-Oxo-4,4-dimethyl-5-androstene-17S-spiro-5'-(2'-oxo-3'-methyl-oxazolidine) are obtained; m.p.: 194°–198° C.

$[\alpha]_D^{20}$ = −69.1° (c=0.5%, in chloroform).

EXAMPLE 13

Preparation of pharmaceutical compositions

Tablets for oral administration, containing 25 mg of active agent, are prepared from the following components:

| | |
|---|---:|
| 2,2-dimethyl-3-oxo-androsta-4,6-diene-17S-spiro-5'-(2'-oxo-3'-methyl-oxazolidine) | 25 mg |
| maize starch | 128 mg |
| polyethylene glycol 6000 | 40 mg |
| talc | 6 mg |
| magnesium stearate | 1 mg |
| average weight: | 200 mg |

The tablets are provided with a film coating or sugar coating.

What we claim is:

1. A compound of the formula (I)

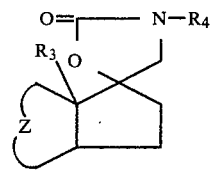

wherein $R_3$ and $R_4$ are each $C_1$ to $C_3$ alky; and
Z is one of the following groups

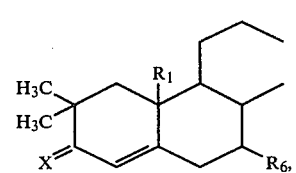
(a)

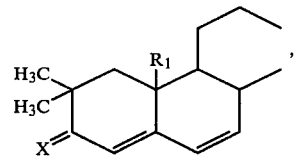
(b)

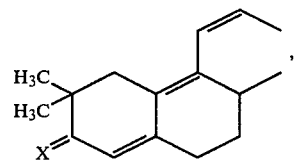
(c)

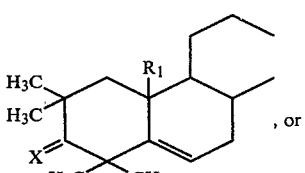
, or (d)

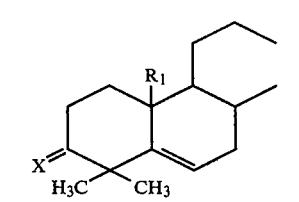
(e)

wherein $R_1$ is hydrogen or methyl;

$R_6$ is hydrogen, $C_1$ to $C_3$ alkylthio or $C_2$ to $C_4$ acylthio; and

X is oxo, hydroxyimino, $C_1$ to $C_3$ alkoxyimino, carboxy-alkoxyimino wherein the alkoxy has 2 to 4 carbon atoms or a salt-converted carboxy-alkoxyimino wherein the alkoxy has 2 to 4 carbon atoms.

2. An aldosterone-antagonizing composition which comprises a compound of the formula (I), wherein $R_1$, $R_2$, $R_3$, $R_4$, $R_5$, $R_{5'}$, $R_6$, X and the dotted lines are as defined in claim 1, together with a pharmaceutically acceptable carrier or auxiliary agent.

3. The compound defined in claim 1 which is 2,2-dimethyl-3-oxo-androsta-4,6-diene-17S-spiro-5'-(2'-oxo-3'-methyl-oxazolidine).

4. The compound defined in claim 1 which is 13β-ethyl-2,2-dimethyl-3-oxo-gona-4,9(10),11-triene-17S-spiro-5'-(2'-oxo-3'-methyl-oxazolidine).

5. A process for the preparation of a compound of the formulae (Ia), (Ib), (Ic) or (Id)

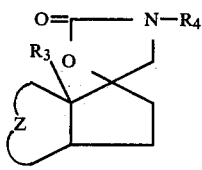 (I)

wherein $R_3$ and $R_4$ are each $C_1$ to $C_3$ alkyl; and
Z is one of the following groups

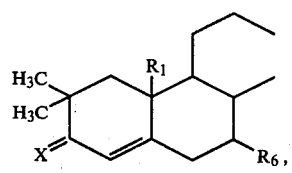 (a)

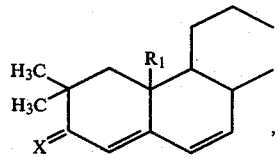 (b)

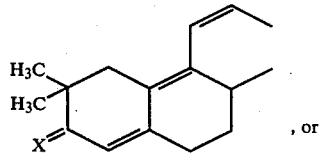 , or (c)

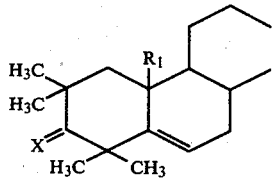 (d)

wherein $R_1$ is hydrogen or methyl;

$R_6$ is hydrogen, $C_1$ to $C_3$ alkylthio, or $C_2$ to $C_4$ acylthio; and X is oxo, hydroxyimino, $C_1$ to $C_3$ alkoxyimino, carboxy-alkoxyimino wherein the alkoxy has 2 to 4 carbon atoms or a salt converted carboxy-alkoxyimino wherein the alkoxy has 2 to 4 carbon atoms, which comprises the steps of:

(a) alkylating a compound of the formula (IIa)

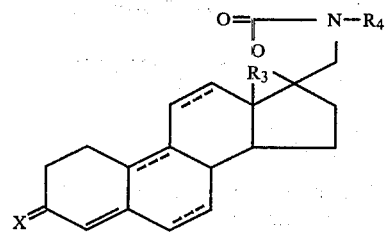

wherein the dotted lines indicate an optional double bond with a methyl halide in the presence of an alkaline agent at a temperature of $-100°$ C. to $-30°$ C. to yield a compound of the formula (I) wherein X is oxo;

(b) in the case where the compound of the formula (I) is a product where X is hydroxy-imino, $C_1$ to $C_3$ alkoxy-imino, carboxy-alkoxyimino wherein the alkoxy has 1 to 3 carbon atoms or a converted carboxylate salt thereof, oximating the compound of the formula (I) where X is oxo with respectively hydroxylamine, a $C_1$ to $C_3$ alkoxyamine, a carboxy-$C_1$ to $C_3$ alkoxy-amine or a salt converted carboxy-$C_1$ to $C_3$ alkoxyamine to yield the desired product; and (c) in the case where the compound of the formula (I) is specifically the compound of the formula (Ia) where $R_6$ is $C_1$ to $C_3$ alkylthio or $C_2$ to $C_4$ acylthio, respectively thioalkylating or thioacylating the compound of the formula (Ib) with a $C_1$ to $C_3$ alkyl mercaptan or $C_1$ to $C_3$ thiocarboxylic acid.

6. The process defined in claim 5, step (a), wherein potassium t-butoxide is used as the alkaline agent.

7. The process defined in claim 5, step (a), wherein methyl iodide is used as the methyl halide.

8. The process defined in claim 5, step (a), wherein an ether is used as the solvent.

9. A process for the preparation of a compound of the formula (Ie)

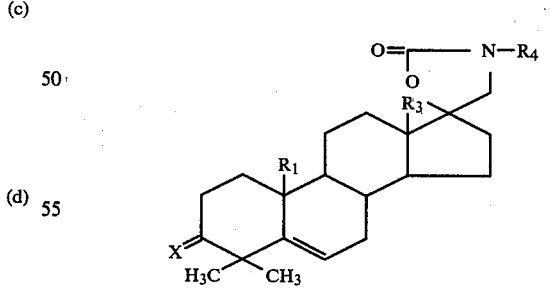

wherein $R_1$ is hydrogen or methyl;

$R_3$ and $R_4$ are each $C_1$ to $C_3$ alkyl; and

X is oxo, hydroxyimino, $C_1$ to $C_3$ alkoxyimino, carboxy-alkoxyimino, wherein the alkoxy has 2 to 4 carbon atoms or a salt-converted carboxy-alkoxyimino wherein the alkoxy has 2 to 4 carbon atoms, which comprises the steps of (a) alkylating a compound of the formula (IIb)

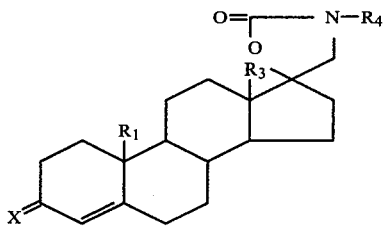

with a methyl halide in the presence of an alkaline agent at a temperature of 0° C. to 30° C. to yield a compound of the formula (Ie) where X is oxo; and (b) in the case where the compound of the formula (Ie) is a product where X is hydroxy-imino, $C_1$ to $C_3$ alkoxy-imino, carboxy-alkoxyimino, wherein the alkoxy has 1 to 3 carbon atoms, or a converted salt of said carboxy-alkoxyimino, oximating the compound of the formula (Ie) where X is oxo with respectively hydroxylamine, a $C_1$ to $C_3$ alkoxyamine, a carboxy-$C_1$ to $C_3$ alkoxyamine or a salt converted carboxy-$C_1$ to $C_3$-alkoxyamine to yield the desired product.

10. The process defined in claim 9, step (a), where potassium t-butoxide is used as the alkaline agent.

11. The process defined in claim 9, step (a), where methyl iodide is used as the methyl halide.

12. The process defined in claim 9, step (a), wherein t-butyl alcohol is employed as a solvent.

13. A method of treatment of a disorder in an animal subject characterized by hyperaldosteronism which comprises administering to said subject an effective amount of a compound as defined in claim 1.

* * * * *